United States Patent
Motoyama et al.

(12) 
(10) Patent No.: US 6,747,172 B1
(45) Date of Patent: Jun. 8, 2004

(54) METHOD FOR PREPARING METHACRYLIC ACID

(75) Inventors: Atsushi Motoyama, Akashi (JP); Isao Nakamura, Ikoma (JP)

(73) Assignee: Nippon Shokubai Co., Ltd., Osaka (JP)

( * ) Notice: Subject to any disclaimer, the term of this patent is extended or adjusted under 35 U.S.C. 154(b) by 575 days.

(21) Appl. No.: 09/684,395

(22) Filed: Oct. 10, 2000

(30) Foreign Application Priority Data

Oct. 12, 1999 (JP) .......................................... 11-289321

(51) Int. Cl.$^7$ .......................... C07C 51/16; B01J 27/19; B01J 27/198; B01J 27/188
(52) U.S. Cl. ...................... 562/549; 502/208; 502/209; 502/210; 502/211
(58) Field of Search ....................... 562/549; 502/208, 502/209, 210, 211

(56) References Cited

U.S. PATENT DOCUMENTS

| 4,260,822 A | | 4/1981 | Krieger et al. |
| 6,060,419 A | * | 5/2000 | Wijesekera et al. |

FOREIGN PATENT DOCUMENTS

| EP | 0-418657 A1 | 3/1991 |
| EP | 0418657 | 3/1991 |
| EP | 0425666 | 5/1991 |
| EP | 0-486291 A1 | 5/1992 |
| EP | 0-771781 A2 | 5/1996 |
| JP | 5562041 | 5/1980 |
| JP | 63145249 | 6/1988 |
| JP | 3106839 | 5/1991 |
| JP | 459738 | 2/1992 |
| JP | 459739 | 2/1992 |
| JP | 5178774 | 7/1993 |
| JP | 6172250 | 6/1994 |
| JP | 7116071 | 12/1995 |
| JP | 81005 | 1/1996 |
| JP | 85820 | 1/1996 |
| JP | 832644 | 3/1996 |
| JP | 912490 | 1/1997 |
| JP | 920700 | 1/1997 |
| JP | 9278680 | 10/1997 |
| JP | 2759376 | 3/1998 |
| JP | 10128112 | 5/1998 |

OTHER PUBLICATIONS

Database WPI, Section Ch, Week 199808, Derwent Publication Ltd., London, GB; An 1998–080757, XP002221541 & JP 09–313943 A (Mitsubishi Chem Corp), Dec. 9, 1997.
Database WPI, Section Ch, Week 198719, Derwent Publication Ltd., London, GB; AN 1987–132022, XP002221542 & JP 62–071533 A (Mitsubishi Chem. Corp.), Apr. 2, 1987.

* cited by examiner

*Primary Examiner*—Johann Richter
*Assistant Examiner*—Paul A. Zucker
(74) *Attorney, Agent, or Firm*—Sherman & Shalloway

(57) ABSTRACT

A method for preparing methacrylic acid at high selectivities and high yields by catalytically vapor phase oxidizing isobutane is provided. In the method, a catalyst comprising (i) a sparingly water-soluble salt of a hetero poly acid and (ii) a composite oxide containing phosphorus, molybdenum and vanadium is used. Component (i) preferably has the element composition (but excluding oxygen) represented by the general formula $A_a B_b Mo_c W_d V_e$ (wherein A is a counter cation, for example cesium, B is the hetero atom of the hetero poly acid, for example silicon, and a, b, c, d and e represent an atomic ratio of the respective elements.), and component (ii) preferably has the element composition represented by the general formula $P_p Mo_q V_r X_s O_t$ (wherein X is for example cesium, and p, q, r, s and t represent an atomic ratio of the respective elements.).

2 Claims, No Drawings

METHOD FOR PREPARING METHACRYLIC ACID

TECHNICAL FIELD TO WHICH THE INVENTION PERTAINS

This invention relates to a method for preparing methacrylic acid. More detailedly, this invention relates to a method for preparing methacrylic acid by catalytically vapor phase oxidizing isobutane.

PRIOR ART

As to a method for preparing methacrylic acid via methacrolein by catalytically vapor phase oxidizing an unsaturated hydrocarbon or tertiary alcohol such as isobutene or tertiary butanol, various methods have been proposed and some of them are industrially adopted.

Also as to a method for preparing methacrylic acid directly by catalytic vapor phase oxidation of isobutane as a saturated hydrocarbon, reports have been made in several publications including Japanese Laid-open Patent Publication No. 55-62041. Many of the methods use a hetero poly acid catalyst containing silicon, phosphorus or arsenic as the hetero atom and molybdenum and/or vanadium as the poly atom as disclosed in Japanese Laid-open Patent Publication No. 62-132832, Japanese Laid-open Patent Publication No. 63-145249, etc. As catalysts other than hetero poly acid catalysts, Mo—V—Sb—Te—O catalysts (Japanese Laid-open Patent Publication No. 9-278680 and Japanese Laid-open Patent Publication No. 10-128112), P—V—Au and/or Ag catalysts (Japanese Laid-open Patent Publication No. 5-178774), etc. have been reported.

However, such prior catalysts have the disadvantage that when the conversion of isobutane is fixed at a low level, the selectivities of methacrylic acid and methacrolein are high to some degree, but when the conversion of isobutane is fixed at a high level, the selectivities of methacrylic acid and methacrolein are lowered, and by-products such as acetic acid and acrylic acid and combustion products such as carbon monoxide and carbon dioxide increase.

Problem to be Solved by the Invention

The object of the invention lies in providing a method for preparing methacrylic acid in high selectivity and high yields by vapor phase oxidizing isobutane in the presence of a catalyst using molecular oxygen or a molecular oxygen-containing gas.

Means for Solving the Problem

The present inventors have found that when, in preparing methacrylic acid by catalytic vapor phase oxidation of isobutane, a catalyst comprising a sparingly water-soluble salt of a hetero poly acid and a composite oxide containing phosphorus, molybdenum and vanadium is used, the above object can be accomplished, and have completed the invention based on the finding.

Thus, according to the invention is provided a method for preparing methacrylic acid which comprises, in preparing methacrylic acid by vapor phase oxidizing isobutane in the presence of a catalyst using molecular oxygen or a molecular oxygen-containing gas, using as the catalyst a catalyst comprising (i) a sparingly water-soluble salt of a hetero poly acid and
(ii) a composite oxide containing phosphorus, molybdenum and vanadium.

MODE FOR CARRYING OUT THE INVENTION

The sparingly water-soluble of a hetero poly acid as component (i) of the catalyst of the invention means a salt of a hetero poly acid with at least one element selected from potassium, rubidium, cesium and thallium. The hetero poly acid is a generic term including typical hetero poly acids such as 12-molybdophosphoric acid, 12-tungstophosphoric acid, 12-molybdosilicic acid, 12-tungstosilicic acid, 12-molybdoarsenic acid and 12-tungstoarsenic acid; these hetero poly acids wherein part of molybdenum and/or tungsten is replaced with vanadium; or these hetero poly acids wherein molybdenum, tungsten or vanadium is coordinated in a mixed state. Such a sparingly water-soluble salt of a hetero poly acid can readily be prepared by adding to an aqueous solution of a hetero poly acid an aqueous solution containing at least one element selected from potassium, rubidium, cesium and thallium. In the invention, the thus obtained sparingly water-soluble salt of a hetero poly acid can be used in a slurry state as the obtained form or in a solid state after the separation of water from the slurry by a treatment such as filtration or centrifugation.

As the hetero poly acids, ones on the market can be used as such or after purification by a known method such as ether extraction, drying or recrystallization. It is also possible to use a hetero poly acid prepared by a known method, for example by acidifying with hydrochloric acid or the like an aqueous solution containing a sodium salt of a metallic acid such as molybdic acid or tungstic acid and sodium phosphate or sodium silicate or the like, heating the solution to make reaction occur, separating the reaction product with an ether as an etherified product from the resulting aqueous solution, and drying the product.

Among the sparingly water-soluble salts of hetero poly acids, preferably used are those having the element composition (but excluding oxygen) represented by the general formula (1), namely $$A_a B_b Mo_c W_d V_e \qquad (1)$$

(wherein A represents a counter cation and is at least one element selected from potassium, rubidium, cesium and thallium, B represents a hetero atom of the hetero poly acid and is at least one selected from silicon, phosphorus and arsenic, Mo, W and V represent molybdenum, tungsten and vanadium respectively which are poly atoms of the hetero poly acid, a, b, c, d and e represent an atomic ratio of the respective elements and when b is 1, a is 3 to 4, c is 0 to 12, d is 0 to 12 and e is 0 to 3, and the total of c, d and e is 12.).

The other component (ii) of the catalyst of the invention is a composite oxide containing phosphorus, molybdenum and vanadium as indispensable components, and it can further contain as other optional components potassium, rubidium, cesium, thallium, magnesium, calcium, strontium, barium, manganese, chromium, iron, cobalt, nickel, copper, zinc, aluminum, tin, lead, antimony, bismuth, yttrium, zirconium, titanium, niobium, tantalum, rhodium, palladium, platinum, silver, lanthanum, cerium, praseodymium, neodymium, etc.

Among them, preferably used are composite oxides represented by the following general formula (2)

$$P_p Mo_q V_r X_s O_t \qquad (2)$$

(wherein P, Mo, V and O represent phosphorus, molybdenum, vanadium and oxygen, respectively, X represents at least one element selected from potassium, rubidium, cesium, thallium, magnesium, calcium, strontium, barium, manganese, chromium, iron, cobalt, nickel, copper, zinc, aluminum, tin, lead, antimony, bismuth, yttrium, zirconium, titanium, niobium, tantalum, rhodium, palladium, platinum, silver, lanthanum, cerium, praseodymium and neodymium, and p, q, r, s and t represent an atomic ratio of the respective elements and when q is 12, p is 1 to 2, r is a number of 2 or less not including 0, s is 0 to 2 and t represents a number of oxygen atoms necessary for satisfying the valences of the respective elements.).

Preparation methods of the composite oxide are not particularly limited, and it can be prepared according to a conventional method. For example, it can be prepared by a method which comprises dissolving or dispersing such raw materials as mentioned below, heating the solution or dispersion to concentrate it to dryness. As phosphorus sources as a raw material, there can be mentioned orthophosphoric acid, pyrophosphoric acid, phosphorous acid, polyphosphoric acid, phosphorus pentoxide, phosphorus pentachloride, sodium phosphate, etc. As molybdenum sources, there can be mentioned molybdenum trioxide, molybdic acid, ammonium paramolybdate, sodium molybdate, etc. As vanadium sources, there can be mentioned, besides vanadium oxide, pentavalent, tetravalent or trivalent vanadium-containing compounds such as metavanadic acid or its salts, pyrovanadic acid or its salts, and vanadium oxyhalides. Hetero poly acids comprising phosphorus, molybdenum and/or vanadium such as molybdophosphoric acid and molybdovanadophosphoric acid can also be used as raw materials.

As raw materials of potassium, rubidium, cesium, thallium, magnesium, calcium, strontium, barium, manganese, chromium, iron, cobalt, nickel, copper, zinc, aluminum, tin, lead, antimony, bismuth, yttrium, zirconium, titanium, niobium, tantalum, rhodium, palladium, platinum, silver, lanthanum, cerium, praseodymium and neodymium as the optional components, there can be mentioned oxides, nitrates, sulfates, carbonates, organic acid salts, alkoxides, organic complex compounds of the respective elements.

There is no particular limitation about methods for preparing the catalyst of the invention, but for example, the following method can be adopted:

(1) a method which comprises separately preparing in advance a sparingly water-soluble salt of a hetero poly acid and a composite oxide containing phosphorus, molybdenum and vanadium and mixing them, or (2) a method which comprises mixing an aqueous solution of a hetero poly acid with an aqueous solution containing at least one element selected from potassium, rubidium, cesium and thallium to prepare a slurry containing the resulting sparingly water-soluble salt of the hetero poly acid, adding to this slurry an aqueous solution separately prepared by dissolving in water raw materials containing phosphorus, molybdenum and vanadium and if necessary optional components, respectively, concentrating the resulting slurry under heating at 50 to 90° C. and stirring to dryness, drying the resulting solid, and calcinating the solid at 300 to 500° C. in an oxygen-containing gas.

Among them, the method of (2) is preferably used.

As to the ratio between component (i) and component (ii) in the catalyst of the invention, it is preferred that the molar ratio $[A_aB_bMo_cW_dV_e]/[P_pMo_qV_rX_sO_t]$ is 1:10 to 10:1, particularly 1:5 to 5:1.

The catalyst of the invention can be used not only in a powdery state, but also in such a state that it is molded alone or together with a carrier such as silica, alumina, titania, zirconia, silicon carbide or ceramics, or it is deposited on such a carrier. As to molding of the catalyst, there is no particular limitation, and it can be molded into an any shape such as spheres, cylinders, rings, arches or saddles by a so far known molding method such as tableting molding or extrusion molding. In the molding, there can be used, as a molding aid, inorganic material such as silica sol, alumina sol, talc or graphite, or organic material such as fatty acid salts. Inorganic fibers can also be used.

In the method of the invention, methacrylic acid can be prepared by vapor phase oxidizing isobutane in the presence of the above catalyst.

Isobutane may contain a small amount of n-butane, butenes, propane, pentane, etc. As the oxygen source used in the vapor phase oxidation, molecular oxygen or a molecular oxygen-containing gas can be used. Specifically, air is preferably used, but pure oxygen alone or diluted with an inert gas such as nitrogen, helium or carbon dioxide can also be used. Usually, the isobutane concentration in the raw material gas is 0.5 to 80% by volume, preferably 1 to 50% by volume, and the volume ratio of oxygen to isobutane is 0.05 to 20, preferably 0.1 to 4. Steam can be made to exist in the raw material gas, and in that case, it is preferred to make steam exist in an amount of 0.1 to 5 volumes of isobutane. When the catalyst is used in a fixed bed, the space velocity (STP) is 500 to 10,000 $h^{-1}$, preferably 800 to 8,000 $h^{-1}$. The reaction temperature is 250 to 550° C., preferably 300 to 450° C. The reaction can be carried out in either of under normal pressure and under imposed pressure, but usually under normal pressure.

EXAMPLES

The invention is further specifically described below according to examples and comparative examples, but the invention is not limited thereto. In the examples and comparative examples, the isobutane conversion, methacrylic acid selectivity and methacrylic acid yield are defined as follows.

Isobutane conversion (% by mol)=(mol number of reacted isobutane/mol number of fed isobutane)×100

Methacrylic acid selectivity (% by mol)=(mol number of formed methacrylic acid/mol number of reacted isobutane)×100

Methacrylic acid one-pass yield (% by mol)=(mol number of formed methacrylic acid/mol number of fed isobutane)×100

Example 1

Silicomolybdic acid ($H_4Si_1Mo_{12}O_{40} \cdot 28H_2O$) (46.6 g) was added to 100 ml of deionized water and dissolved under stirring, and a solution obtained by dissolving 11.7 g of cesium nitrate ($CsNO_3$) in 70 ml of deionized water was added dropwise to obtain a slurry containing the sparingly water-soluble salt of the hetero poly acid (Liquid A).

Separately, 5.19 g of 85% by weight phosphoric acid, 2.73 g of vanadium pentoxide and 51.82 g of molybdenum trioxide were dispersed in 450 ml of deionized water, and the dispersion was refluxed under stirring for 3 hours to obtain a dark-brown uniform solution (Liquid B).

To Liquid A were added Liquid B and a solution obtained by dissolving 12.7 g of cesium nitrate ($CsNO_3$) in 80 ml of deionized water. The resulting slurry was concentrated under heating at 70° C. and stirring to dryness, and dried at 120° C. for 20 hours in a nitrogen stream. The resulting solid was pulverized and sieved to obtain 16 to 30 mesh of particles. These particles were calcined at 380° C. for 4 hours in a stream of the mixed gas of air: nitrogen of 1:3 by volume ratio to obtain a catalyst of the invention having a composition of 0.4 $(Cs_3Si_1Mo_{12})/0.6(P_{1.5}Mo_{12}V_1Cs_{2.17})$ by atom ratio excluding oxygen.

This catalyst (4 g) was filled into a stainless steel-made flow-type reactor, and oxidation reaction of isobutane was carried out under the following conditions. The results are shown in Table 1.

Raw material gas: Mixed gas of isobutane/air/steam (=7.5/67.5/25 volume ratio)

Space velocity: 5,600 $h^{-1}$

Reaction temperature: 350° C.

Example 2

A catalyst of the invention having a composition of 0.4 $(Cs_3P_1Mo_{12})/0.6 (P_{1.5}Mo_{12}V_1Cs_{2.17})$ by atom ratio excluding oxygen was obtained in the same manner as in Example 1 except that phosphomolybdic acid $(H_3P_1Mo_{12}O_{40}.25H_2O)$ was used in place of silicomolybdic acid in preparation of Liquid A in Example 1. Using this catalyst, vapor phase oxidation of isobutane was carried out under the same conditions as in Example 1. The results are shown in Table 1.

Comparative Example 1

A catalyst for comparison having a composition of $P_{1.5}Mo_{12}V_1Cs_{2.17}$ by atom ratio excluding oxygen was obtained in the same manner as in Example 1 except for not using Liquid A but using Liquid B alone. Using this catalyst, vapor phase oxidation of isobutane was carried out under the same conditions as in Example 1. The results are shown in Table 1.

Comparative Example 2

A catalyst for comparison having a composition of $Cs_3Si_1Mo_{12}$ by atom ratio excluding oxygen was obtained in the same manner as in Example 1 except for not using Liquid B but using Liquid A alone. Using this catalyst, vapor phase oxidation of isobutane was carried out under the same conditions as in Example 1. The results are shown in Table 1.

Example 3

A catalyst of the invention having a composition of 0.4 $(Cs_3P_1Mo_{12})/0.6(P_{1.5}Mo_{12}V_1Cs_{2.17}Zn_{0.2})$ by atom ratio excluding oxygen was obtained in the same manner as in Example 1 except that a solution obtained in advance by dissolving 1.8 g of zinc nitrate $(Zn(NO_3)_2.6H_2O)$ in Liquid B was used in place of Liquid B. Using this catalyst, vapor phase oxidation of isobutane was carried out under the same conditions as in Example 1. The results are shown in Table 1.

Examples 4 to 8

Catalysts of the invention were obtained in the same manner as in Example 3 except that 1.7 g of manganese nitrate $(Mn(NO_3)_2.6H_2O)$ (Example 4), 2.4 g of iron nitrate $(Fe(NO_3)_2.9H_2O)$ Example 5), 1.7 g of cobalt nitrate $(Co(NO_3)_2.6H_2O)$ (Example 6), 1.7 g of nickel nitrate $(Ni(NO_3)_2.6H_2O)$ (Example 7) or 1.4 g of copper nitrate $(Cu(NO_3)_2.3H_2O)$ (Example 8) was used in place of zinc nitrate in Example 3. Using each catalyst, vapor phase oxidation of isobutane was carried out under the same conditions as in Example 1. The results are shown in Table 1.

Example 9

Vapor phase oxidation of isobutane was carried out under the same manners as in Example 1 except that the space velocity and reaction temperature were changed to 2,800 $h^{-1}$ and 340° C., respectively, in Example 1. The results are shown in Table 1.

Example 10

Vapor phase oxidation of isobutane was carried out under the same conditions as in Example 9 using the catalyst prepared in Example 3. The results are shown in Table 1.

TABLE 1

| | Catalyst composition | Isobutane conversion (mol by %) | Methacrylic acid selectivity (% by mol) | Methacrylic acid one-pass yield (% by mol) |
|---|---|---|---|---|
| Example 1 | 0.4 $(Cs_3Si_1Mo_{12})/0.6 (P_{1.5}Mo_{12}V_1Cs_{2.17})$ | 11.4 | 48.4 | 5.5 |
| Example 2 | 0.4 $(Cs_3P_1Mo_{12})/0.6 (P_{1.5}Mo_{12}V_1Cs_{2.17})$ | 10.8 | 48.7 | 5.3 |
| Comparative Example 1 | $P_{1.5}Mo_{12}V_1Cs_{2.17}$ | 6.6 | 40.4 | 2.6 |
| Comparative Example 2 | $Cs_3Si_1Mo_{12}$ | 5.7 | 21.2 | 1.2 |
| Example 3 | 0.4 $(Cs_3Si_1Mo_{12})/0.6 (P_{1.5}Mo_{12}V_1Cs_{2.17}Zn_{0.2})$ | 14.7 | 48.0 | 7.1 |
| Example 4 | 0.4 $(Cs_3Si_1Mo_{12})/0.6 (P_{1.5}Mo_{12}V_1Cs_{2.17}Mn_{0.2})$ | 13.0 | 45.2 | 5.9 |
| Example 5 | 0.4 $(Cs_3Si_1Mo_{12})/0.6 (P_{1.5}Mo_{12}V_1Cs_{2.17}Fe_{0.2})$ | 20.0 | 42.1 | 8.4 |
| Example 6 | 0.4 $(Cs_3Si_1Mo_{12})/0.6 (P_{1.5}Mo_{12}V_1Cs_{2.17}Co_{0.2})$ | 13.9 | 42.4 | 5.9 |
| Example 7 | 0.4 $(Cs_3Si_1Mo_{12})/0.6 (P_{1.5}Mo_{12}V_1Cs_{2.17}Ni_{0.2})$ | 16.0 | 43.5 | 7.0 |
| Example 8 | 0.4 $(Cs_3Si_1Mo_{12})/0.6 (P_{1.5}Mo_{12}V_1Cs_{2.17}Cu_{0.2})$ | 18.4 | 38.4 | 7.1 |
| Example 9 | 0.4 $(Cs_3Si_1Mo_{12})/0.6 (P_{1.5}Mo_{12}V_1Cs_{2.17})$ | 25.3 | 40.2 | 10.2 |
| Example 10 | 0.4 $(Cs_3Si_1Mo_{12})/0.6 (P_{1.5}Mo_{12}V_1Cs_{2.17}Zn_{0.2})$ | 25.8 | 41.5 | 10.7 |

Effect of the Invention

The catalysts used in the invention show higher catalytic activity even at lower reaction temperatures compared with conventional catalysts. Hereby, according to the method of the invention, methacrylic acid can be prepared from isobutane at high selectivities and high yields and with good reproducibility.

What is claimed is:

1. A method for preparing methacrylic acid by vapor phase oxidation of isobutane with molecular oxygen or a molecular oxygen-containing gas in the presence of a catalyst, characterized in that said catalyst comprises:
   (i) a sparingly water-soluble salt of a heteropolyacid, and
   (ii) a composite oxide containing phosphorus, molybdenum and vanadium, and that said catalyst has been prepared by a method which comprises mixing an aqueous solution of a heteropolyacid with an aqueous solution containing at least one element selected from potassium, rubidium, cesium and thallium to prepare a slurry containing a resulting sparingly water-soluble salt of the heteropolyacid, adding to this slurry an aqueous solution separately prepared by dissolving in water raw materials containing phosphorus, molybdenum and vanadium and, if necessary, optional components, concentrating the resulting slurry under heating and stirring to dryness, drying the resulting solid, and calcinating the solid in an oxygen-containing gas.

2. The method according to claim 1 wherein said catalyst comprises the component (i) and the component (ii) in such a ratio that the molar ratio of the former to the latter is 1:10 to 10:1.

* * * * *